United States Patent [19]

Penniman et al.

[11] Patent Number: 4,661,225
[45] Date of Patent: Apr. 28, 1987

[54] METHOD AND APPARATUS FOR MEASURING THE ELECTROPHORETIC MOBILITY OF MIGRATING PARTICLES

[75] Inventors: John G. Penniman, Carmel; Ryder O. FitzGerald, Brewster, both of N.Y.

[73] Assignee: Paper Chemistry Laboratory, Inc., Carmel, N.Y.

[21] Appl. No.: 743,180

[22] Filed: Jun. 10, 1985

[51] Int. Cl.$^4$ .............................................. G01N 27/26
[52] U.S. Cl. ............................ 204/183.3; 204/299 R
[58] Field of Search ........................ 204/299 R, 183.3

[56] References Cited

U.S. PATENT DOCUMENTS

| | | | |
|---|---|---|---|
| 3,454,487 | 7/1969 | Riddick | 204/299 |
| 3,708,402 | 1/1973 | Bean | 204/299 R |
| 3,764,512 | 10/1973 | Greenwood et al. | 204/299 |
| 3,793,180 | 2/1974 | Flower et al. | 204/299 |
| 3,909,380 | 9/1975 | Day et al. | 204/180 |
| 4,046,667 | 9/1977 | Goetz | 204/299 |
| 4,239,612 | 12/1980 | Goetz | 204/299 R |

FOREIGN PATENT DOCUMENTS 148244 9/1982 Japan ............................ 204/299 R Primary Examiner—John F. Niebling
Assistant Examiner—Nam X. Nguyen
Attorney, Agent, or Firm—Pennie & Edmonds

[57] ABSTRACT

An apparatus for measuring the electrophoretic mobility of migrating particles in a suspending medium under the influence of an applied electric field comprising an electrophoresis chamber, means for illuminating the electrophoresis chamber, a microscope having an objective lens system and an ocular lens system, said microscope being positioned to view the electrophoresis chamber along an optical path extending from the electrophoresis chamber through the objective lens system and toward the ocular lens system, means for generating moving bands of visible energy into the ocular lens system of the microscope, means for adjusting the speed of the moving bands of visible energy; and means for determining the speed of the moving bands.

A method for measuring the electrophoretic mobility of migrating particles in a suspending medium under the influence of an applied electric field which comprises introducing a suspension medium containing colloidal particles into an electrophoresis chamber, positioning the electrophoresis chamber on a spring-loaded plate mechanism, illuminating the contents of the electrophoresis chamber, viewing the illuminated colloidal particles in the electrophoresis chamber through a microscope, applying a voltage potential across the electrodes of the electrophoresis chamber, to cause migration of the colloidal particles, generating moving bands of visible energy in the ocular lens system of the microscope, adjusting the speed of the moving bands until they match the speed of the migrating particles, and determining the speed of the moving bands and thus the corresponding mobility of the colloidal particles.

22 Claims, 1 Drawing Figure

METHOD AND APPARATUS FOR MEASURING THE ELECTROPHORETIC MOBILITY OF MIGRATING PARTICLES

BACKGROUND OF THE INVENTION

1. Field of the Invention

The invention relates to an apparatus for measuring the mobility of dispersed particles in a liquid medium, from which the zeta potentials of those particles may be calculated.

2. Description of the Prior Art

The term "zeta potential" is understood in colloidal chemistry as an indicator of the electrophoretic mobility of particulate matter colloidally suspended or dispersed in a fluid medium. The electrophoretic mobility, in turn, is an indication of the velocity of the particles through the solution due to the effect of an applied electric field.

With regard to colloidal particles suspended in a fluid medium, the suspended particles are considered electrically neutral. That is, each particle is surrounded by a double layer of electrical or electrostatic charges, the inner layer of which is immediately adjacent to and fixed to the particle, while the outer layer, which possesses a charge opposite to that of the inner layer, is attracted by the surface charge and extends out into the solution for some distance.

The zeta potential, therefore, is not measured on the surface of a particle but rather at what is known as the "slipping" or "shear" plane where the net difference in force between the particle and the bulk solution which surrounds it is small enough so that the particle may move independently within an electrophoretic cell when an electric potential is applied across the electrodes of the cell. This migration occurs because the charged groups and ions adsorbed on the surface of the colloidal particles produce a non-uniform distribution of ions in solution near the particle-liquid interface.

The stability of a particle suspended in a bulk medium is directly related to the zeta potential of the particle. Stable particles remain dispersed whereas unstable particles tend to agglomerate and eventually precipitate out of the solution. The higher the zeta potential, the more stable the system is since highly charged particles repel one another and remain dispersed.

In some cases, such as the manufacture of paint, pharmaceuticals and cosmetics, it is desirable to maximize the zeta potential so as to achieve greater stability. Conversely, in situations involving the treatment of waste water or during the manufacture of paper, it is important to minimize this potential, as this leads to the agglomeration of the colloidal particles and the settling out of the flocculate formed thereby.

Various means have been utilized to measure the zeta potentials of colloidal particles suspended in a liquid medium. U.S. Pat. No. 3,454,487 to Riddick discloses a manually operated microelectrophoresis apparatus, wherein the electrophoretic mobility, i.e. the velocity of the particles per unit field strength, is measured in an electrophoretic cell which consists of sample receiving chambers connected by a liquid-flow communication passageway.

This measurement is performed utilizing an ocular micrometer or distance scale which is inserted into the eyepiece of a microscope. The particles are timed as they cross a fixed distance in the observation chamber of the electrophoretic cell under a D.C. electric field of known strength. This method is time consuming and tedious to employ since repeated operations are necessary to accurately calibrate the instrument and determine the zeta potential in a sample bulk medium.

In order to facilitate more rapid and efficient measurements of electrophoretic mobility, attempts were made to develop a "semi-automatic" microelectrophoresis apparatus as disclosed in U.S. Pat. No. 3,764,512 to Greenwood et al. In this apparatus, a coherent light beam from a laser is caused to intermittently scan a path located on the stationary layer of an electrophoresis chamber by means of a mirror galvanometer at a rate equal to the migration rate of the particles in the chamber. The operator views the migrating particles in the chamber through a microscope and simultaneously adjusts the scanning rate of the mirror galvanometer by adjusting a potentiometer in the galvanometer control circuit until the scanning laser beam appears to visually track the migrating particles as viewed through the microscope. Via appropriate scaling circuitry interacting with the galvanometer drive circuit and the circuit supplying the voltage drop across the chamber, a value for electrophoretic mobility or zeta potential may automatically be displayed through suitable means, such as an electronically operated digital readout.

U.S. Pat. No. 3,793,180 to Flower et al. discloses a fully automated system capable of measuring zeta potential, particle size distribution, total charge density and other distribution functions of aqueous suspensions. A laser beam is provided in the instrument and is focused on the particles in the sample solution which are contained in an electrophoretic cell. A reticle or grating is positioned such that the reflection of the laser beam from the particles passes through the reticle to a photo-tube placed on the other side of the reticle. Then, as the particles move through the solution the photo-tube is intermittently illuminated through the reticle and, as a result, generates a train of electric pulses whose frequency is directly proportional to the velocity of the particles. Since the frequency of the electrical signal is a measurement of the particle velocity, it is also a measure of zeta potential. The advantage of a fully automated system is that it serves to reduce the human error associated with the manual operation of the prior methods.

In U.S. Pat. No. 3,909,380 to Day, a television camera or other equivalent image sensor, such as a photosensitive array utilizing a suitable lens system, observes the fluid within an electrophoresis cell which is illuminated by the cold light of a fiberoptic source in order to prevent the production of convection currents in the medium.

The suspended particles are magnified by a microscope and the image is projected onto the monitor screen. A reference pattern is superimposed onto the monitor and the sweep speed of the reference pattern is then manually adjusted to match the speed of any single particle or group of particles on the monitor screen. The sweep speed of the reference pattern may then be converted to a zeta potential signal which must be corrected for the temperature of the sample.

Finally, U.S. Pat. No. 4,046,667 to Goetz describes an electrophoresis chamber, a circuit for impressing a voltage across the chamber, a light beam to illuminate a portion of the chamber, and a microscope including an objective lens system and an eyepiece for viewing illuminated particles migrating relative to a suspending medium within the chamber under the influence of the applied voltage. Within the microscope, between the objective lens and the eyepiece, is a movable optical prism driven by a galvanometer, the drive circuit of which includes an adjustable potentiometer for controlling the rate and direction of movement of the optical prism.

A circuit connected to the galvanometer drive circuit and the circuit applying the voltage potential across the chamber are adapted to develop a signal proportional to the electrophoretic mobility or zeta potential of the migrating particles when the rate of movement of the optical prism is adjusted such that it cancels the transfer velocity of the migrating particles. The particles then appear stationary when observed through the eyepiece of the microscope. Because the movable optical prism is located inside of the microscope, between the objective lens and the eyepiece, it is possible to employ an electrophoresis chamber having a rectangular cross-sectional shape such that its height is significantly less than its width. By virtue of this geometry the electrophoresis chamber is rendered relatively impervious to thermodynamic effects. The electrophoresis chamber, which is constructed of three relatively thin flat plates, also includes means for mounting and supporting a pair of spaced electrodes; as well as means for avoiding entrapment of air bubbles while being filled with a sample.

Applicants have now discovered an improved apparatus and method for measuring the mobility of colloidal particles suspended in a liquid medium which avoids the drawbacks of the prior art.

SUMMARY OF THE INVENTION

The invention relates to an apparatus for measuring the electrophoretic mobility of migrating particles in a suspending medium under the influence of an applied electric field which comprises an electrophoresis chamber, means for illuminating the electrophoresis chamber, a microscope, a means for generating moving bands of visible energy, means for adjusting the speed of the moving bands of visible energy and means for determining the speed of these bands.

The microscope consists of an objective lens system and an ocular lens system, and it is positioned so as to view the electrophoresis chamber along an optical path extending from the electrophoresis chamber, through the objective lens system and toward the ocular lens system. The moving bands of visible energy are directed into the ocular lens system of the microscope.

The apparatus is utilized by introducing a suspension medium, such as distilled water, containing colloidal particles into an electrophoresis chamber, positioning the electrophoresis chamber on a spring-loaded plate mechanism in order to assure that the proper plane is in microscopic focus, illuminating the contents of the electrophoresis chamber and viewing the illuminated colloidal particles in the electrophoresis chamber through the ocular lens of the microscope. A voltage potential is then applied across the electrodes of the electrophoresis chamber in order to cause migration of the colloidal particles while moving bands of visible energy are also generated and directed into the ocular lens system of the microscope. The speed of the moving bands is adjusted until it matches the speed of the migrating particles and this speed is then determined as corresponding to the mobility of the colloidal particles.

In one embodiment of the invention, the moving bands of visible energy are generated by the sequential illumination of a linear array of light sources and subsequently directed into the optical path of the microscope. Preferably, the light sources may be light emitting diodes ("LEDs").

In an alternate embodiment of the present invention, the means for adjusting the speed of the moving bands of visible energy is a manually adjustable potentiometer. Advantageously, this potentiometer is a slide potentiometer which is capable of increasing or decreasing the speed of the moving bands of visible energy by being moved from side to side by the operator of the apparatus.

In a further embodiment, the electrophoresis chamber is produced by molding an optical grade of thermoplastic into the desired configuration. The chamber should have a substantially rectangular cross-sectional configuration wherein its width is substantially smaller than its height. In an alternate embodiment, the electrophoresis chamber may be reproducibly molded and factory calibrated such that these chambers are interchangeable as well as disposable after one or a number of uses.

In another embodiment, once the operator matches the speed of the moving bands of visible energy to that of the migrating colloidal particles, the resultant velocity is indicated on display means, such as an LED digital display.

BRIEF DESCRIPTION OF THE DRAWING

Further benefits and advantages of the invention will become apparent from a consideration of the following description given with reference to the accompanying drawing figure which specifies and shows preferred embodiments of the present invention, and wherein:

The single FIGURE is a schematic representation of an instrument constructed to incorporate the principles of the present invention.

DETAILED DESCRIPTION OF THE PREFERRED EMBODIMENTS

Figure 1:
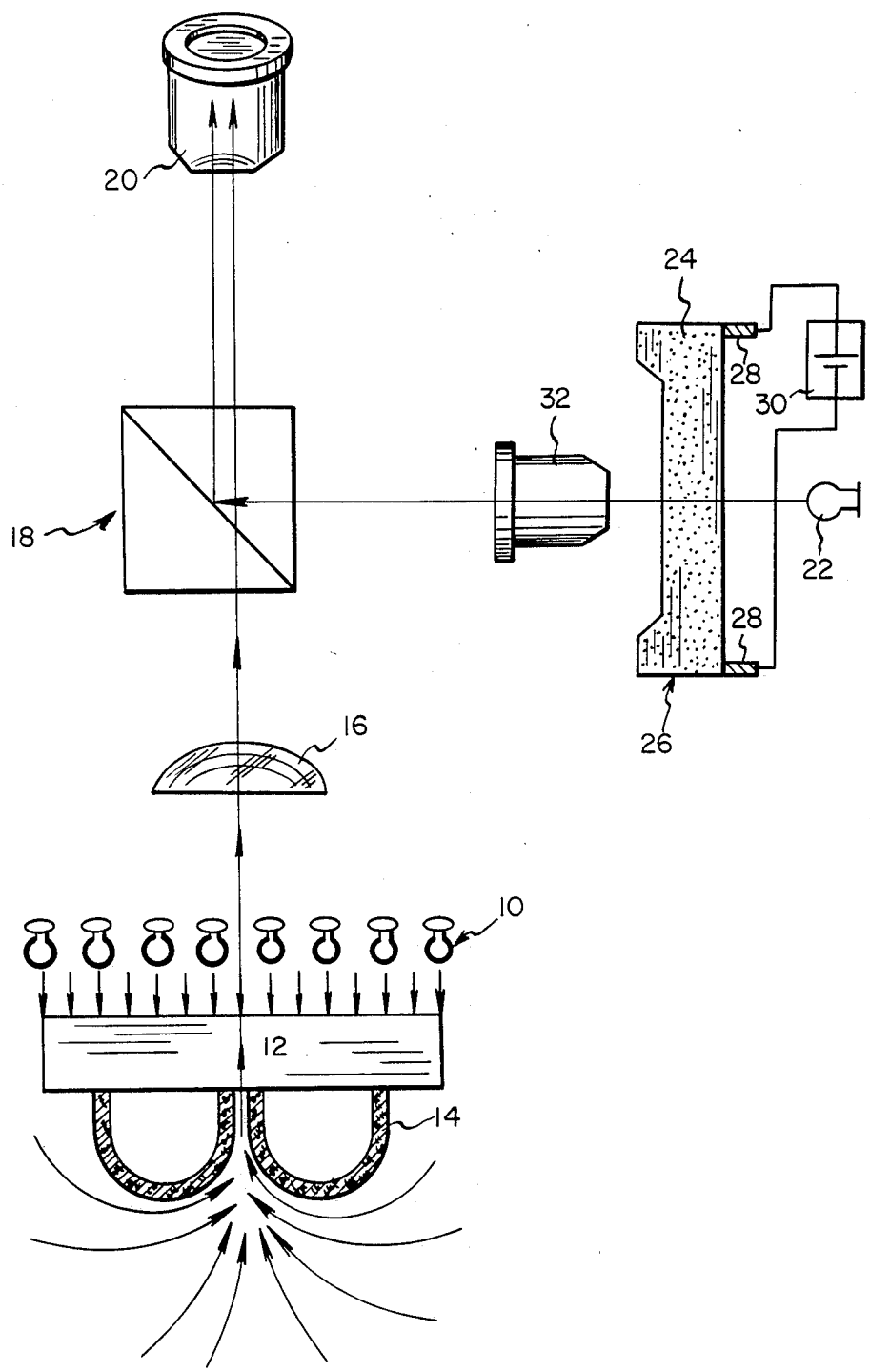

Electrophoresis is a technique well-known in the prior art. The applicant does not claim to have invented this technique but those skilled in the art will recognize that its use by applicant in the process and apparatus of the present invention provides adequate evidence of the novelty of the present invention.

As shown in the schematic representation, the illumination from a linear array of light sources 10 impinges upon optical scanner 12 which then focuses the light through optical fibers 14 and directs the light into the optical path of the microscope. The light passes through cylindrical lens 16 which converts the circular spots of light into bands of light, and then into cube beam splitter 18. After passing through the nonmirrored surface of the beam splitter 18, the bands enter the ocular lens 20 of the microscope where they may be viewed by the eye of an observer.

Concurrently with the operation described above, a single light source 22 is lit in order to illuminate colloidally suspended particles 24 which have been introduced into electrophoresis chamber 26. A voltage potential is then applied across electrodes 28 of electrophoresis chamber 26 by voltage source 30 in order to cause the colloidally suspended particles 24 to migrate through the suspending medium towards one of the electrodes 28.

Advantageously, the interior surfaces of the electrophoresis chamber may be coated with a non-ionic coating such as one which uses a methylcellulose, base. This coating acts to reduce the electroendosmotic effects due to the electrical charge associated with the chamber wall material.

The image of the colloidal particles 24 is then focused by objective lens 32 of the microscope before being deflected by a mirrored surface on cube beam splitter 18. The image of the particles then appears in the ocular lens 20 of the microscope.

It will be appreciated by those skilled in the art that the components illustrated in the schematic representation, with the exception of the electrophoresis chamber, are all maintained in predetermined, fixed positions in alignment with respect to the optical paths of the microscope. Since the electrophoresis chamber 26 is removable, a spring-loaded plate mechanism is provided to ensure that this chamber 26 is returned to its predetermined position and proper orientation in the optical path. This arrangement further ensures that the particles will be properly in focus when viewed through the microscope.

A preferred embodiment of the present invention utilizes light-emitting diodes as the light sources 10, 22 because LED's produce low thermal energy. Light sources such as these generate "cold light" i.e., illumination without the concurrent production of significant thermal energy that can cause convection currents in the suspension medium within the electrophoresis cell 26 and thus interfere with the operator's attempt to obtain a valid particle mobility reading. Any number of LEDS which produces the desired effect may be used, however, sixteen have been found to produce the requisite effect while maintaining the compactness of the device.

The images of the colloidal particles 24 and the bands of light caused by the sequential illumination of the light sources 10 overlap in the ocular lens 20 of the microscope.

In a preferred embodiment of the present invention, after superimposing the image of the moving bands of light onto the images of the colloidal particles 24 in the ocular lens 20 of the microscope, the speed of the moving bands is adjusted, by means of a potentiometer or other means for adjusting the resistance of the circuit, to match that of the colloidal particles 24. The resultant speed of the moving light bands, therefore, is equivalent to the electrophoretic mobility of the colloidal particles. This value may then be displayed in some manner, preferrably by means of a light-emitting diode digital display or with the use of a strip-chart or other recording means.

Although the most basic function of the present apparatus is to provide measurements of particle mobility, which are useful in various industries, the apparatus of the present invention, when equipped with the appropriate circuitry, is capable of converting this value into a measurement of zeta potential, in millivolts upon taking into account the temperature at which the measurement was made.

This conversion may also be performed manually by multiplying the particle mobility value obtained with applicant's apparatus by an appropriate multiplier from Table I below, once again taking into account the temperature at which the mobility measurement was made.

TABLE I

| SAMPLE TEMPERATURE (°C.) | MULTIPLIER |
|---|---|
| 10 | 17.62 |
| 11 | 17.21 |
| 12 | 16.80 |
| 13 | 16.42 |
| 14 | 16.05 |
| 15 | 15.70 |
| 16 | 15.36 |
| 17 | 15.04 |
| 18 | 14.72 |
| 19 | 14.43 |
| 20 | 14.14 |
| 21 | 13.86 |
| 22 | 13.60 |
| 23 | 13.34 |
| 24 | 13.09 |
| 25 | 12.85 |
| 26 | 12.62 |
| 27 | 12.40 |
| 28 | 12.19 |
| 29 | 11.98 |
| 30 | 11.78 |

EXAMPLES

The following examples demonstrate various conversions of particle mobility values into zeta potential values. These examples are set forth for the purpose of illustration only and are not to be construed as limiting the scope of the invention in any manner.

EXAMPLE I

At 20° C., a mobility reading of −2.00 would equal a zeta potential of −28.28 mV because:

$$-2.00 \times 14.14 = -28.28 \text{ mV}$$

EXAMPLE II

At 25° C., a mobility reading of −2.20 would equal a zeta potential of −28.27 because:

$$-2.20 \times 12.85 = -28.27 \text{ mV}$$

The advantages of the present invention also include its compact design and ease of portability for convenient transport to job sites in the field where a bulkier, more fragile apparatus would not be practical, as well as the inclusion of solid-state electronic circuitry which eliminates the need for any moving parts. Small sample sizes may be analyzed and, as the instrument is factory calibrated, this procedure need not be repeated before each use, as with the apparatus of the prior art.

If required, however, the size of the instrument may be scaled upward and its options extended to include such functions as zeta potential conversions where there is a need to have such an apparatus readily available at a plant site such as when measurements of this type must be performed as a matter of routine during the normal manufacturing process.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

We claim:

1. An apparatus for measuring the electrophoretic mobility of migrating particles in a suspending medium under the influence of an applied electric field comprising:
   an electrophoresis chamber;
   means for illuminating the electrophoresis chamber;
   a microscope having an objective lens system and an ocular lens system, said microscope being positioned to view the electrophoresis chamber along an optical path extending from the electrophoresis chamber through the objective lens system and toward the ocular lens system;
   means for generating moving bands of visible energy within the ocular lens system of the microscope;
   means for adjusting the speed of the moving bands of visible energy; and
   means for determining the speed of the moving bands.

2. The apparatus of claim 1 wherein the moving bands of visible energy are generated by the sequential illumination of a linear array of light sources.

3. The apparatus of claim 2 wherein the light sources are light emitting diodes.

4. The apparatus of claim 1 wherein the means for illuminating the electrophoresis chamber is a light emitting diode.

5. The apparatus of claim 1 wherein the means for adjusting the speed of the moving bands of visible energy is a manually adjustable potentiometer.

6. The apparatus of claim 5 wherein the manually adjustable potentiometer is a slide potentiometer.

7. The apparatus of claim 1 wherein the electrophoresis chamber has a substantially rectangular cross-sectional configuration.

8. The apparatus of claim 7 wherein the width of said electrophoresis chamber is substantially smaller than its height.

9. The apparatus of claim 1 wherein the electrophoresis chamber is produced by molding an optical grade of thermoplastic into the desired configuration.

10. The apparatus of claim 1 wherein a spring-loaded plate mechanism positions the electrophoresis chamber so that the proper plane is in microscopic focus.

11. The apparatus of claim 1 further comprising means for displaying the electrophoretic mobility of the particles in the electrophoresis chamber.

12. The apparatus of claim 11 wherein the means for displaying the electrophoretic mobility of the particles comprises a light emitting diode digital display.

13. The apparatus of claim 12 further comprising means for converting a particle mobility value into a value representing the zeta potential of the particle.

14. A method for measuring the electrophoretic mobility of migrating particles in a suspending medium under the influence of an applied electric field which comprises:
   introducing a suspension medium containing colloidal particles into an electrophoresis chamber;
   positioning the electrophoresis chamber on a spring-loaded plate mechanism;
   illuminating the contents of the electrophoresis chamber;
   viewing the illuminated colloidal particles in the electrophoresis chamber through a microscope;
   applying a voltage potential across the electrodes of the electrophoresis chamber, to cause migration of the colloidal particles;
   generating moving bands of visible energy with in the ocular lens system of the microscope;
   adjusting the speed of the moving bands until they match the speed of the migrating particles; and
   determining the speed of the moving bands and thus the corresponding mobility of the colloidal particles.

15. The method of claim 14 which further comprises generating the moving bands of visible energy by sequentially illuminating a linear array of light sources.

16. The method of claim 14 wherein the contents of the electrophoresis chamber are illuminated by means a light emitting diode.

17. The method of claim 14 wherein the speed of the moving bands of visible energy is adjusted by means of a manually adjusted potentiometer.

18. The method of claim 14 which further comprises suspending the colloidal particles in distilled water.

19. The method of claim 14 which further comprises indicating the electrophoretic mobility of the colloidal particles on display means.

20. The method of claim 19 further comprising converting a particle mobility value into a value representing the zeta potential of the particle.

21. An apparatus for measuring the electrophoretic mobility of migrating particles in a suspending medium under the influence of an applied electric field comprising:
   an electrophoresis chamber;
   means for illuminating the electrophoresis chamber;
   a microscope having an objective lens system and an ocular lens system, said microscope being positioned to view the electrophoresis chamber along an optical path extending from the electrophoresis chamber through the objective lens system and toward the ocular lens system;
   means for generating moving bands of visible energy within the optical path of the microscope, said generating means including means for directing said bands into the ocular lens system of the microscope;
   means for adjusting the speed of the moving bands of visible energy; and
   means for determining the speed of the moving bands.

22. A method for measuring the electrophoretic mobility of migrating particles in a suspending medium under the influence of an applied electric field which comprises:
   introducing a suspension medium containing colloidal particles into an electrophoresis chamber;
   illuminating the colloidal particles of the suspension medium;
   viewing the illuminated colloidal particles through a microscope;
   applying a voltage potential across a pair of electrodes of the electrophoresis chamber to cause migration of the colloidal particles;
   generating moving bands of visible energy within the optical path of the microscope;
   directing the moving bands of visible energy into the ocular lens of the microscope;
   adjusting the speed of the moving bands to match the speed of the migrating particles; and
   determining the speed of the moving bands and thus the corresponding mobility of the colloidal particles.

* * * * *